United States Patent [19]
Bacus et al.

[11] Patent Number: 5,473,706
[45] Date of Patent: Dec. 5, 1995

[54] METHOD AND APPARATUS FOR AUTOMATED ASSAY OF BIOLOGICAL SPECIMENS

[75] Inventors: James W. Bacus, Hinsdale; James V. Bacus, Lombard, both of Ill.

[73] Assignee: Becton Dickinson and Company, Franklin Lakes, N.J.

[21] Appl. No.: 213,389

[22] Filed: Mar. 14, 1994

Related U.S. Application Data

[63] Continuation of Ser. No. 764,336, Sep. 23, 1991.

[51] Int. Cl.⁶ ............................................. G06K 9/00
[52] U.S. Cl. .............................. 382/133; 356/39; 359/391
[58] Field of Search .................................. 382/1, 6, 100, 382/128, 133, 134; 364/413.07, 413.08, 413.13; 356/39, 40; 422/55; 359/391, 393; 348/79

[56] References Cited

U.S. PATENT DOCUMENTS

| | | | |
|---|---|---|---|
| 3,805,028 | 4/1974 | Morton | 235/92 PC |
| 3,833,796 | 9/1974 | Fetner et al. | 235/151.3 |
| 3,851,972 | 12/1974 | Smith et al. | 356/72 |
| 4,122,518 | 10/1978 | Castleman et al. | 364/300 |
| 4,175,860 | 11/1979 | Bacus | 356/39 |
| 4,362,386 | 12/1982 | Matsushita et al. | 356/39 |
| 4,404,683 | 9/1983 | Kobayashi et al. | 364/413.08 |
| 4,453,807 | 6/1984 | Faulkner et al. | 359/391 |
| 4,487,910 | 6/1989 | Sakuraba et al. | 382/6 |
| 4,702,595 | 10/1987 | Motscher et al. | 382/6 |
| 4,741,043 | 4/1988 | Bacus | 356/39 |
| 4,761,075 | 8/1988 | Matsushita et al. | 356/39 |
| 4,836,667 | 6/1989 | Ozeki | 359/393 |
| 4,887,892 | 12/1989 | Bacus | 356/39 |
| 4,959,796 | 9/1990 | Hidaka et al. | 356/39 |
| 4,998,284 | 3/1991 | Bacus et al. | 382/6 |
| 5,000,554 | 3/1991 | Gibbs | 382/6 |
| 5,018,209 | 5/1991 | Bacus | 364/413.08 |
| 5,086,476 | 2/1992 | Bacus | 364/413.08 |
| 5,109,929 | 4/1992 | Bacus et al. | 382/6 |
| 5,134,662 | 7/1992 | Bacus et al. | 382/6 |
| 5,311,426 | 5/1994 | Donohue et al. | 356/39 |

FOREIGN PATENT DOCUMENTS

| | | |
|---|---|---|
| 0317139 | 5/1989 | European Pat. Off. . |
| 0365928 | 5/1990 | European Pat. Off. . |
| 0421736 | 4/1991 | European Pat. Off. . |
| wo8500223 | 1/1985 | WIPO . |
| wo9106911 | 5/1991 | WIPO . |

*Primary Examiner*—Joseph Mancuso
*Assistant Examiner*—Gerard DelRosso

[57] ABSTRACT

An apparatus and method for automated assay of biological specimens positioned on microscope slides. The apparatus comprises an interactive optical subsystem for viewing the biological specimen on the slide and for producing an interactive video signal corresponding to the viewed image. An automated optical subsystem includes a single high power microscope objective for scanning a rack of slides, portions of which having been previously identified for assay in the interactive optical subsystem. The system also includes a processor for processing the interactive and automatic video signals from the two optical subsystems. The processor receives the automatic video signal and performs biological assay functions upon it.

12 Claims, 9 Drawing Sheets

METHOD AND APPARATUS FOR AUTOMATED ASSAY OF BIOLOGICAL SPECIMENS

This application is a continuation of application Ser. No. 07/764,336, filed Sep. 23, 1991.

BACKGROUND OF THE INVENTION

This invention relates to a system for performing an assay of biological cell samples, and more particularly, for providing an automated method and arrangement of measuring attributes of the image fields and cells of slide mounted tissue samples.

The diagnosis and/or prognosis of a patient's condition frequently includes the removal of a cell sample, such as a tissue mass, from the patient. Although an attending physician may have good intuition regarding the patient's diagnosis and/or prognosis, confirmation of the diagnosis with histological examination of the cell sample removed from the patient is necessary. The histological examination entails cell staining procedures which allow the morphological features of the cells to be seen relatively easily in a light microscope. A pathologist, after having examined the stained cell sample, makes a qualitative determination of the state of the tissue and reaches a conclusion regarding the prognosis for the patient. While this diagnostic method has a long history, it is somewhat lacking in scientific rigor since it is heavily reliant on the subjective judgment of the pathologist and it is extremely time-consuming.

The alternative to the strictly qualitative and time-consuming human analysis is automated cell analysis where the pathologist uses specialized equipment to perform the analysis. Flow cytometry equipment is one type of automated apparatus for cell analysis. With flow cytometry, mass tests are performed in gross on a specimen cell population without a researcher being able to exclude or include certain data of the population. The specimen is measured "as is" without really knowing what cells are being measured and how many. Important single cell data or data from relatively small groups of cells are lost in the overall averaging of a specimen. Further, relatively large amounts of a specimen have to be used to provide a required level of accuracy. Again, small changes in individual cells or small cell populations cannot be discerned.

Commercially available general purpose flow cytometers are very expensive and can handle only liquid blood specimens or tissue disaggregated specimens. Additionally, flow cytometers are incapable of working on standard tissue sections or using conventional microscope slides which are the preferred specimen forms of pathology laboratories.

Although the automation of cell analysis using microscope slide cell samples is exceedingly difficult, such has been automated to a human-machine interactive level. One such method and apparatus is described in U.S. Pat. No. 4,471,043 to Bacus, for Method And Apparatus For Image Analysis Of Biological Specimens. Cell samples are attached to slides and an operator adjusts the system optics to view desired image fields of the cell sample. The operator then selects and classifies particular cell objects of the sample. After such operator action, the automated equipment quantitatively measures particular attributes of the selected and classified cell objects and records a digital representation of the optical image. The measured attributes can be reported on a per object basis or on an accumulated basis, and the stored image representations can later be read from memory for review.

The automation of analysis of slide cell samples as described in U.S. Pat. No. 4,471,043 has provided many advantages over both the historical pure human analysis and the automated flow cytometry analysis. Large amounts of human operator time and judgment are still required to complete a tissue section assay. A need exists, however, for improvements in the automation of analysis of slide cell samples, and particularly, for slide tissue samples.

SUMMARY OF THE INVENTION

An apparatus and method for automated assay of biological specimens positioned on microscope slides comprises an interactive optical subsystem for viewing the biological specimen on the slide and for producing an interactive video signal corresponding to the viewed image. An automated optical subsystem includes a single high power microscope objective for scanning a rack of slides, portions of which having been previously identified for assay in the interactive optical means. The system also includes a processor subsystem for processing the interactive and automatic video signals from the two optical subsystems. The processor receives the automatic video signal and performs biological assay functions upon it.

It is a principal aspect of the present invention to provide an apparatus for automated assay of biological specimens having a low magnification interactive optical subsystem for interactively scanning the fields of microscope slides having biological specimens positioned thereon.

It is another aspect of the present invention to provide an apparatus for automated assay of biological specimens which apparatus can process a plurality of slides automatically without operator intervention.

It is a still further aspect of the present invention to provide an apparatus for automated assay of biological specimens having both a low magnification interactive optical portion and a high magnification and the automated optical section for high power automated assay.

Other aspects and advantages of the present invention will become apparent to one of ordinary skill in the art upon a perusal of the following specification and claims in light of the accompanying drawings.

DETAILED DESCRIPTION OF THE PREFERRED EMBODIMENT

The preferred embodiment disclosed herein is used for the assay or quantitation of biological specimens specifically estrogen and progesterone in tissue samples. The tissue sample staining and measuring techniques for the estrogen/ progesterone assay are described in detail in U.S. Pat. No. 5,008,185, issued Apr. 16, 1991 to Bacus which is hereby incorporated by reference. The tissue sample assay is performed using a two-color optical system to enhance the optical characteristics of stained tissue samples. It will be apparent to those skilled in the art that many inventive features of the disclosed embodiment may be employed for other types of cell analysis e.g., DNA quantification and that other types of optical apparatus e.g., single color could be employed.

Figure 1:
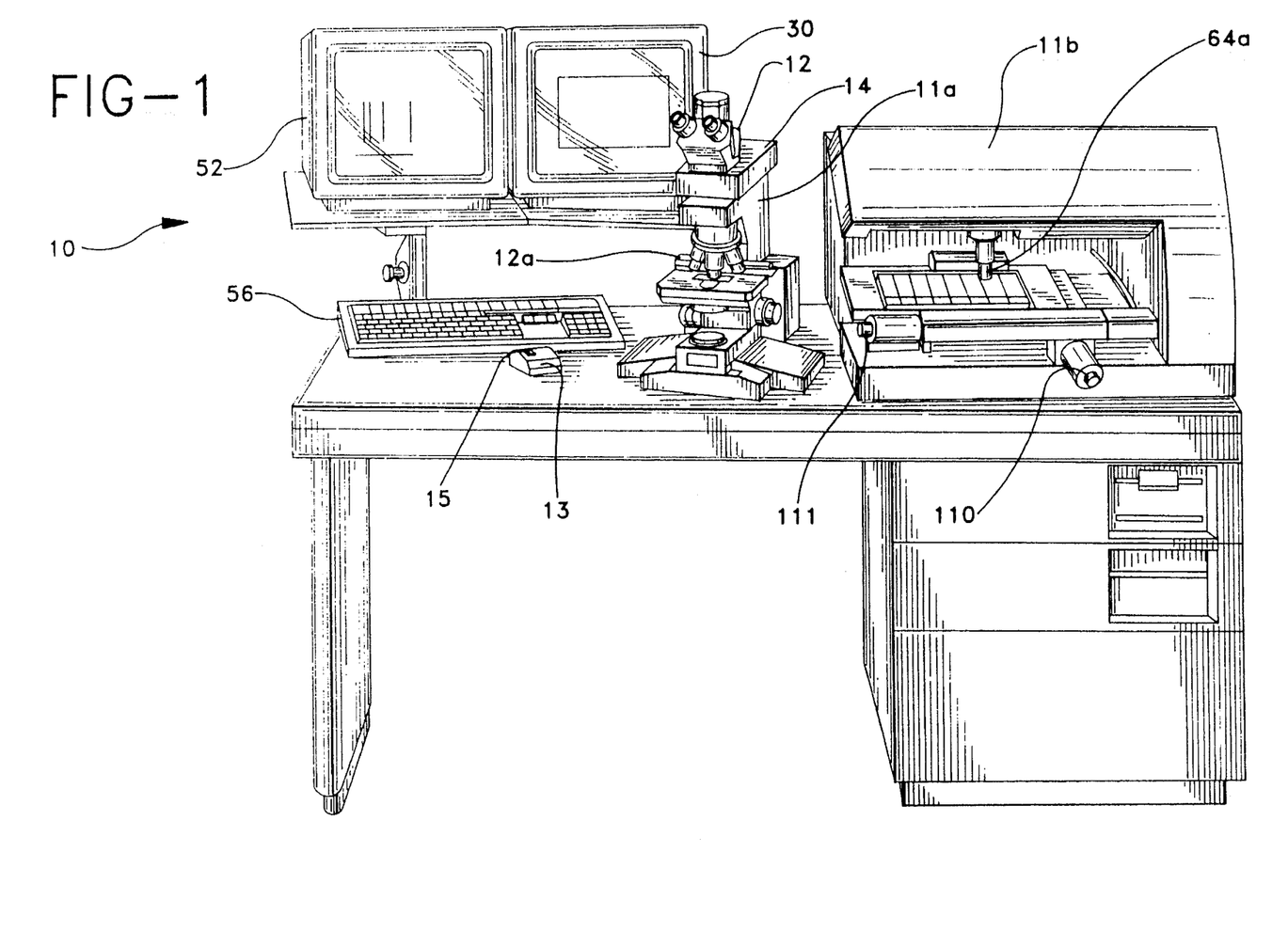
FIG. 1 is a perspective view of an apparatus for assaying biological specimens embodying the present invention.
Figure 1A:
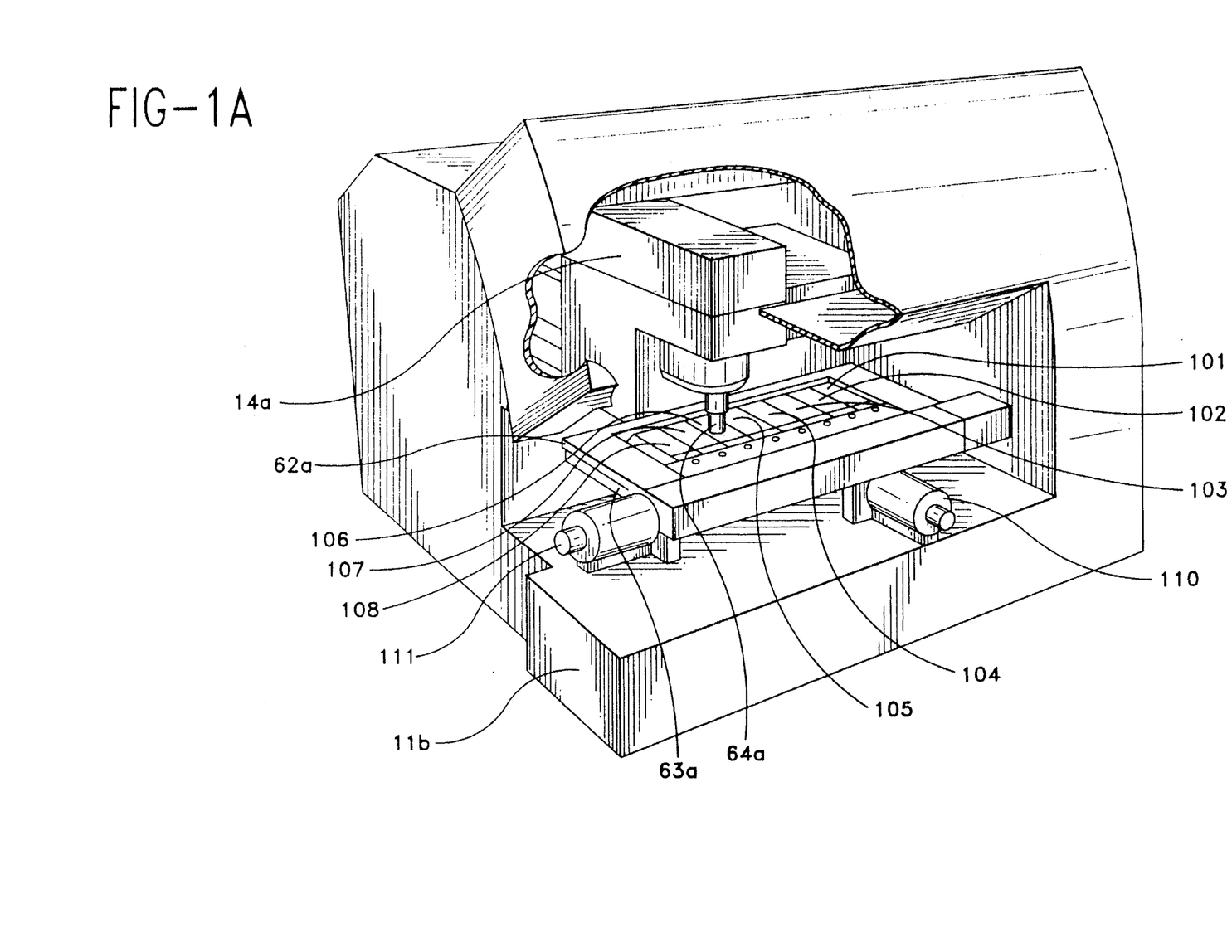
FIG. 1A is a perspective view, having portions broken away, of an automatic optical input subsystem of the apparatus for assaying biological specimens shown in FIG. 1.
Figure 2:
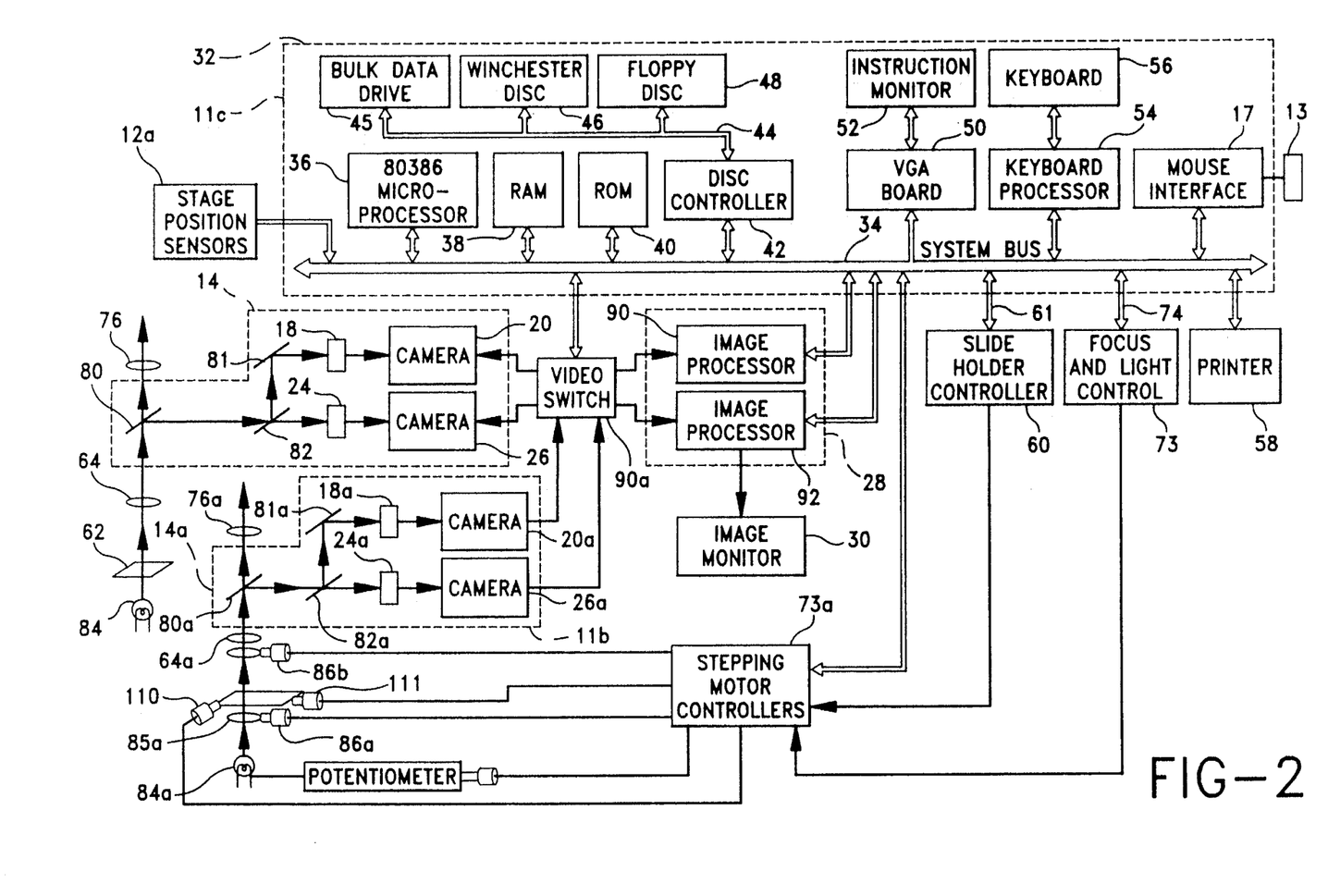
FIG. 2 is a block diagram of the apparatus shown in FIG. 1.

An apparatus for assaying biological specimens, and embodying the present invention and generally identified by numeral 10 is shown in perspective view in FIG. 1 and in block diagram form in FIG. 2. The apparatus 10 comprises an interactive optical input system 11a primarily for use in low power scanning of microscope slides of biological specimens to select fields for later analysis. An automated assay processing system 11b also comprises a portion of the apparatus for scanning up to eight slides at once at relatively high magnification for performing biological assays on the slide.

A processor system 11c receives signals from the optical units for later image processing.

The interactive optical system 11a comprises an optical microscope 12, which may be of any conventional type, but in this embodiment, is a Riechart Diastar. An optical conversion module 14 is mounted on the microscope 12 to enhance the optically magnified image of cell samples viewed with the microscope 12. The optical conversion module 14, as may best be seen in FIG. 2, includes a beam-splitting prism 80 which conveys approximately 90% of the light into optical conversion module 14 and passes the remaining 10% to a microscope eyepiece 76. The light transmitted into module 14 is fed to a dichroic beam-splitter 82 which reflects a portion of the light to a television camera 20 via a red filter 18 and a mirror 81. The remaining portion of the light is filtered by a dichroic beam-splitter 82 and fed to a television camera 26 through a green filter 24. The dichroic beam-splitter 82 selectively passes light having wavelengths greater than approximately 560 nanometers to the filter 18 and having a wavelength of less than 560 nanometers to the filter 24. Thus, the dichroic beam-splitter 82 acts as a first color filter before the light reaches the color filters 18 and 24. Red filter 18 is a 620±20 nanometer bandpass optical transmission filter which provides a high contrast image to the camera 20. As shown in FIG. 2, the camera 20 then generates an NTSC image signal which is fed through an optical signal switch 90a to an image processor 90 of an image processor module 28 (FIG. 2).

Green filter 24 is a 500±20 nanometer narrow bandpass optical transmission filter which provides a high contrast image to a camera 26. The camera 26 then feeds an NTSC image signal through the optical signal switch 90a to an image processor 92. Both of the image processors 90 and 92 contain analog to digital converters for converting the analog NTSC signals to a digitized 384 by 485 array pixel image. The center 256 by 256 array of pixels from this digitized image is then stored within frame buffers internal to the image processors 90 and 92. The visual image represented by the 256 by 256 array of pixels is referred to as an image field.

During assembly of the apparatus of FIG. 1, and from time to time thereafter, if necessary, the optical elements of conversion module 14 are adjusted so that each camera 20 and 26 receives the same optical image and each pixel of the digitized pixel arrays produced by processors 90 and 92, presents the same region of a viewed optical field.

Each of the image processors 90 and 92 is a Model AT428 from the Data Cube Corporation, and includes six internal frame buffers. The image processors 90 and 92 are connected to a system bus 34 of a computer 32. The frame buffers of image processors 90 and 92 are mapped into the address space of a microprocessor 36 in computer 32 to provide easy access for image processing. Additionally, an image monitor 30 is connected to image processor 92 and displays a cell sample image field stored in a predetermined one of the frame buffers. The storage of an image field representation into the predetermined frame buffer is described later herein.

The automatic optical conversion module 11b, as may best be seen in FIG. 2, includes a beam-splitting prism 80a which conveys approximately 90% of the light into optical conversion module 14a and passes the remaining 10% to a microscope eyepiece (not shown). The light transmitted into module 14a is fed to a dichroic beam-splitter 82a which reflects a portion of the light to a television camera 20a via a red filter 18a and a mirror 81a. The remaining portion of the light is filtered by a dichroic beam-splitter 82a and fed to a television camera 26a through a green filter 24a. The dichroic beam-splitter 82a selectively passes light having wavelengths greater than approximately 560 nanometers to the filter 18a and having a wavelength of less than 560 nanometers to the filter 24a. Thus, the dichroic beam-splitter 82a acts as a first color filter before the light reaches the color filters 18a and 24a. Red filter 18a is a 620±20 nanometer bandpass optical transmission filter which provides a high contrast image to the camera 20a. As shown in FIG. 2, the camera 20a then generates an NTSC image signal which is fed through the optical signal switch 90 to the image processor 90 of the image processor module 28 (FIG. 2). Green filter 24a is a 500±20 nanometer narrow bandpass optical transmission filter which provides a high contrast image to a camera 26a. The camera 26a then feeds an NTSC image signal through the optical signal switch 90a to the image processor 92.

The microprocessor 36 of computer 32 is an Intel 80486 microprocessor which is connected to the system bus 34. The optical switch 90a, under control of the microprocessor 36, selects the signal from interactive unit 11a or automatic unit 11b to be fed to the image processors 90 and 92. A random access memory 38 and a read only memory 40 are also connected to the system bus 34 for storage of program and data. A disk controller 42 is connected by a local bus 44 to a Winchester disk drive 46 and to a floppy disk drive 48 for secondary information storage. Advantageously, local bus 44 is connected to a moveable media bulk data drive 45 such as an optical write once read many times (WORM) drive for image field recording and retrieval.

A video conversion board 50, in this embodiment a VGA board, is connected to the system bus 34 to control an instruction monitor 52 connected to the VGA board 50. Operational information such as selection menus and reports of analysis are displayed on monitor 52. A keyboard processor 54 is connected to the system bus 34 to interpret signals from a keyboard 56 connected to the keyboard processor 54. Input signals to microprocessor 36 are also generated by a hand control drive (mouse) 13 having a control button 15. Signals from mouse 13 and its button 15 are conveyed to bus 34 via a mouse interface 17. A printer 58 is connected to the system bus 34 for communication with microprocessor 36.

The automated image input subsystem 11b of apparatus 10 performs automated X-Y slide positioning, image focusing, light intensity adjustment and light color balancing functions. The X-Y slide position controlling apparatus is shown in FIGS. 1, 1A, 3 and 4, and includes a slide holder 62a capable of holding eight microscope slides 101 through 108 in side-by-side relationship. Slide holder 62a is movably attached to the stage 65a of microscope objective 64a by means of a slide holder base 63a. The portion of slide holder 62a positionable with respect to microscope objective 64a is controlled by an X position stepper motor 110 and a Y position stepper motor 111 which are mechanically attached to base 63a. The stepper motors 110 and 111 are of the type known in the art which respond to pulse signals from a slide holder position controller 60. The actual X and Y positions of the slide holder 62 are sensed by an X position sensor 68 and a Y position sensor 66, respectively, which substantially continuously report position information to slide holder controller 60. In the present embodiment the slide holder 62, base 63, and position sensors 66 and 68 including limit switches and numbered 110 and 111 comprise a commercially available unit available from Marzhauser Wetzlar GmbH Model EK8B-S4 with Model MCL-3 control units.

Figure 3:
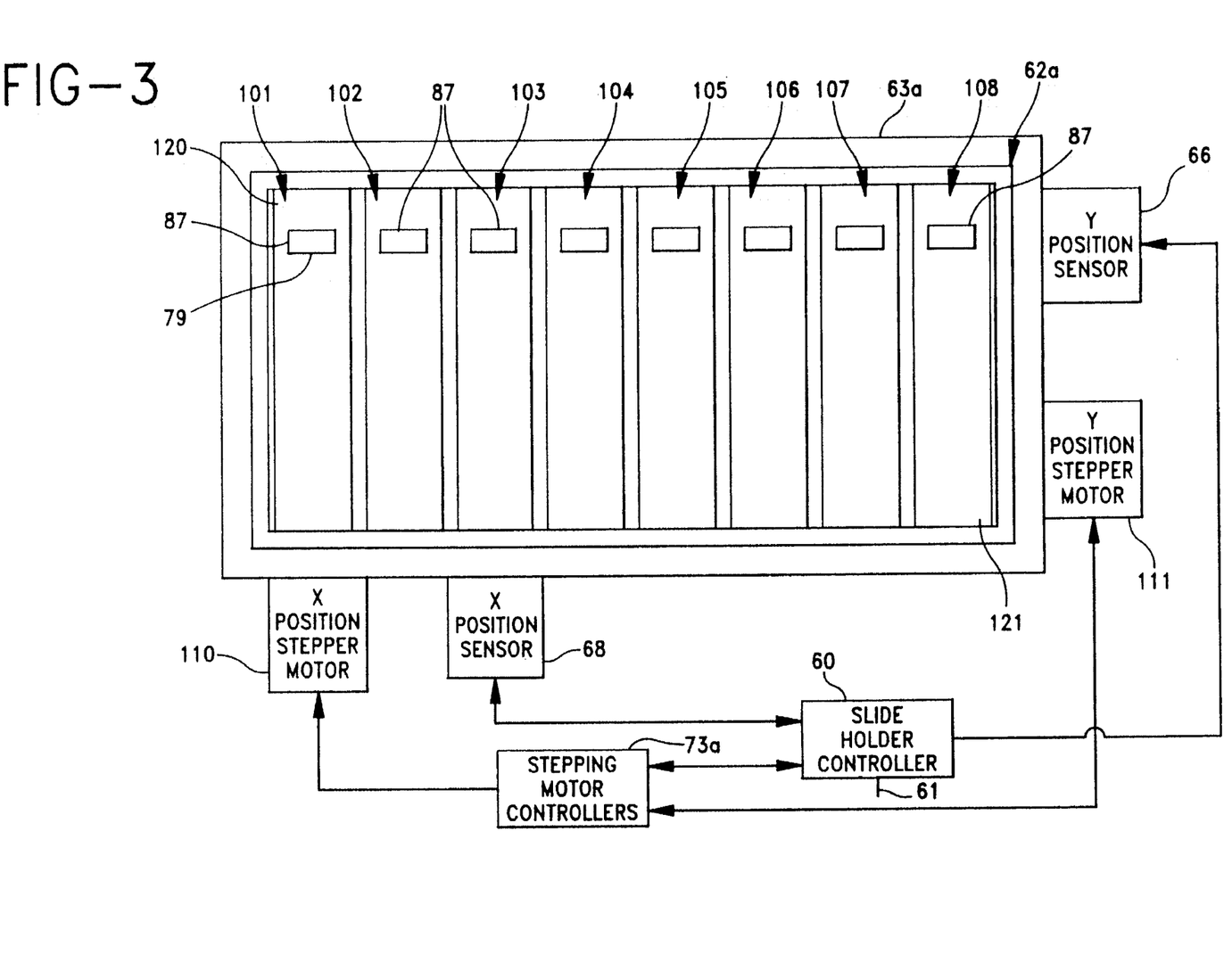
FIG. 3 shows a slide holder and associated control equipment of the apparatus shown in FIG. 1.

Responsive to appropriate stepper motor control signals, the slide holder base 63a is capable of placing substantially all of each of slides 101 through 108 under the objective 64a. Slide holder position controller 60 is connected to system bus 34 by means of a communication path 61. Microprocessor 36, as discussed later herein, transmits commands to slide holder position controller 60 specifying an X and Y position to place under the microscope objective 64a. Slide holder position controller 60 responds to such commands by transmitting to the X and Y stepper motors 110 and 111 the appropriate sets of pulse signals to move the slide holder 62a to the desired X-Y position. The actual position of slide holder 62a is checked by slide holder position controller 60 during and at the completion of movement. The slide holder position controller 60 also maintains an internal record of the X and Y position of the slide holder 62a which internal record can be read by microprocessor 36 via bus 34 and communication path 61.

Figure 4:
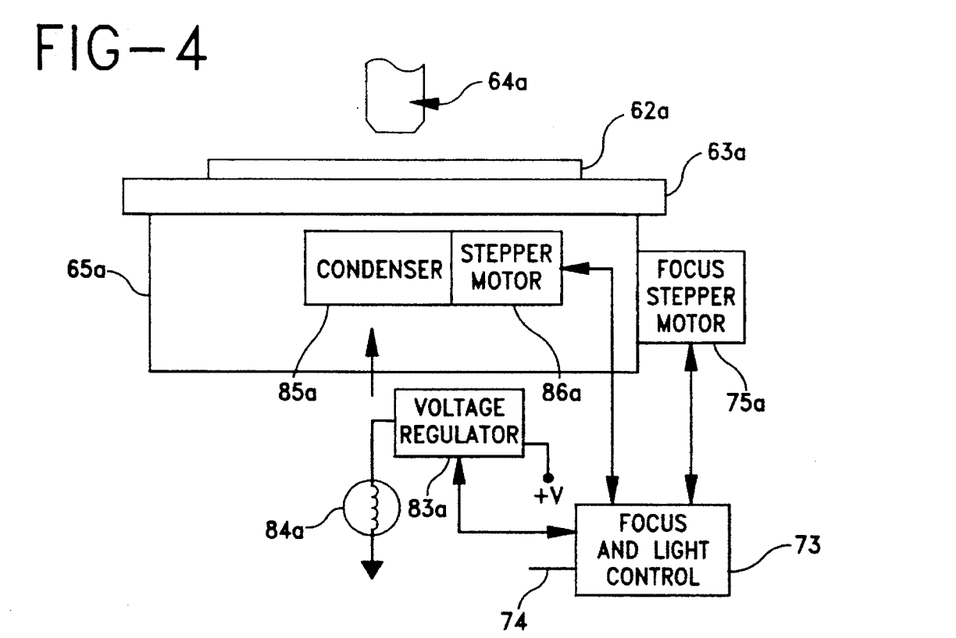
FIG. 4 is a block diagram view of focus and light control portions of the apparatus shown in FIG. 1.

The apparatus 10 also includes a focus and light controller 73 which controls the light intensity and color balance from the light source 84a, as well as the focus of the image field presented to microscope 12. Microprocessor 36 communicates with focus and light controller 73, via the system bus 34 and a communication path 74, to control the focus and light properties. FIG. 4 is a functional block diagram of focus and light controller 73 and its connection to objective 64a and to bus 34. The objective 64a includes a focus stepper motor 75a, which is controlled by focus and light controller 73 through the stepper motor controller 73a to raise and lower the stage 62a, and thereby raise and lower the microscope slides 101 through 108 carried by slide holder 62a. Microprocessor 36 includes a focus routine which is periodically performed during tissue analysis. When the focus routine is entered, microprocessor 36 reviews a digital representation of an image field from the image processors 90 and 92, and issues a command to focus and light controller 73, to raise or lower the stage by a specified amount. Focus and light controller 73 responsively transmits to focus stepper motor 82a electrical signals to implement the requested stage movement. By continued checking of the quality of the image field and adjustment of the up and down position of the slide holder 62a, microprocessor 36 brings the upper surface of the slide under the objective 64a into focus.

Microprocessor 36 also stores a target value for the light intensity which is to be maintained during tissue sample analysis. This stored light intensity value is used by microprocessor 36 in conjunction with an intensity function to regulate the intensity of light from light source 84a. When the intensity function of microprocessor 36 is enabled, the light intensity as represented by image fields from image processors 90 and 92 is determined. Any departure from the stored target light intensity value is corrected by sending intensity control commands to focus and light controller 73 which responds thereto by controlling a voltage regulator to increase or decrease the voltage applied to light source 84a. Voltage regulator 83 may be, for example, a standard rotatable voltage regulator which is rotated by a stepper motor operating under the control of electrical signals from focus and light controller 73.

The analysis performed in the present embodiment relies on a two-color system. For accuracy of measurement, it is important that the two-colors observed by cameras 20 and 26 be of substantially the same intensity. The microprocessor 36 includes a color balance function, which is called to match the intensities of the red and green colors applied to cameras 20 and 26 by light source 84. Objective 64a has associated with it a condenser 85a, which is controlled by a stepper motor 86a, electrically connected to focus and light controller 73. When in the color balance function, microprocessor senses color imbalance by comparing the image field of image processor 90 with that of image processor 92. Microprocessor 36 sends color balance adjustment commands to focus and light controller 73 in response to color imbalance and through a process of repeated comparison and color balance adjustment commands achieves a color balance suitable for tissue sample analysis.

Figure 5:
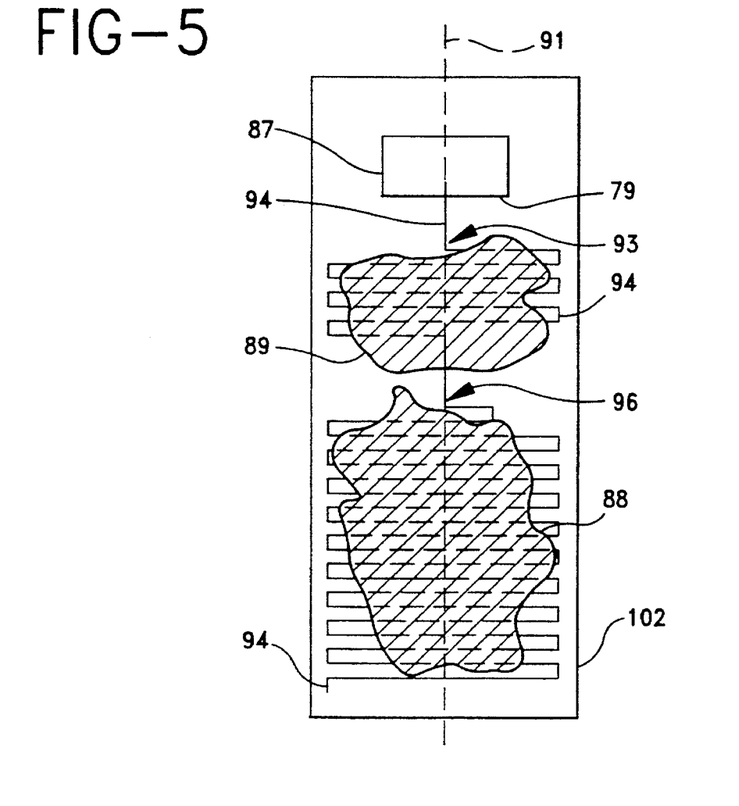
FIG. 5 is a plan view of a tissue section microscope slide for use with the apparatus of FIG. 1.

FIG. 5 shows a representation slide e.g., 102 which has been prepared for analysis in accordance with the embodiment. The slide 102 includes a dark line outline 87 of a rectangle near one end thereof. The rectangle 87, which is printed in substantially the same position on all slides is used during focus and light adjustment routines and during slide preparation to identify the placement of tissue samples.

The method of quantitating nuclear proteins of the present embodiment includes providing specimen 88 cell objects on slide 102 and staining them with an optical enhancement factor which specifically binds to the nuclear protein. The stain is then viewed with the image analysis system 10 to measure the optical density of the stain for intensity measurement and to locate the areas in which stain is found for distribution measurement. Because the intensity of the staining relates to the quantity of the nuclear proteins, measurement of the different optical densities of the stain permits a direct measurement of the quantity of the proteins. In the preferred embodiment, control cell objects 89 are placed on a reference section of the slide 102 to provide a normalization or reference optical density for the staining. Further, one or several counterstains can be used to further distinguish among several features of the cell objects.

No actual marks except rectangle 87 appear on the slides 101–108 to differentiate the control cell objects 89 from the specimen 88. However, the slide should be prepared such that the control cell objects 89 overlap the longitudinal center line of the slide (denoted by a dotted line 91 in FIG. 5) and that the control cell objects 89 are closer to the rectangle 87 than is the specimen 88. Similarly, the specimen 88 should be positioned overlapping the longitudinal center line and farther from rectangle 87 than the control cell objects 89.

Figure 7:
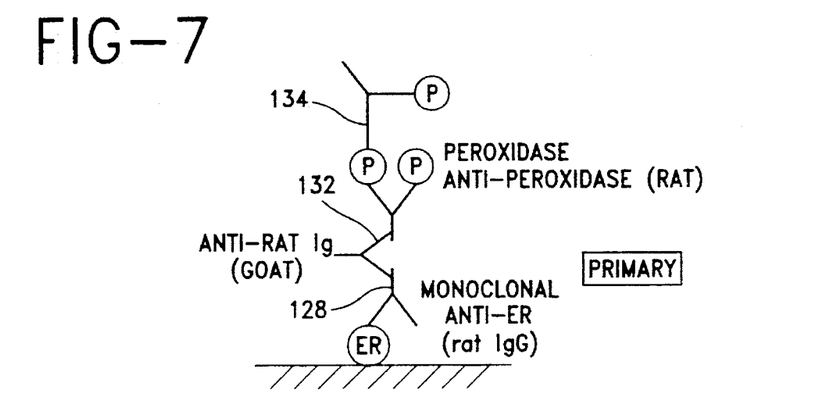
FIGS. 7 and 8 are schematic views of the biological specimen preparation prior to assay.
Figure 8:
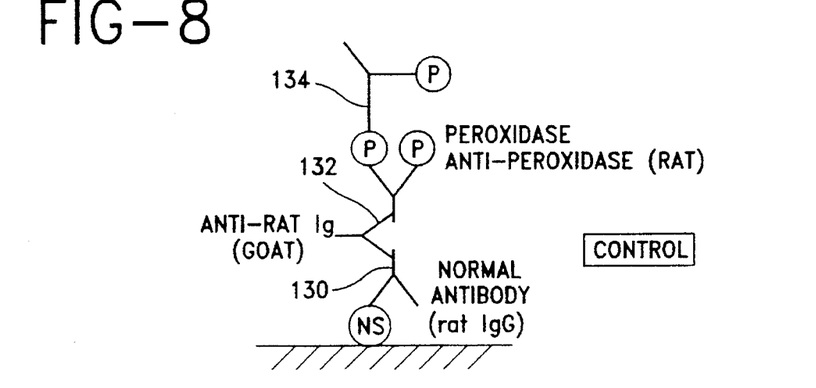

Preferably, in one particular embodiment, the staining method employs a sensitive peroxidase-antiperoxidase technique for visualization of estrogen or progesterone receptors in specimens through the use of monoclonal antibodies directed specifically against those receptors. A diagrammatic representation of the process on the microscopic level is illustrated in FIGS. 7 and 8. Two portions of a human tumor specimen containing a cell population from which the estrogen receptors are to be measured are placed on the two separate sections of the slide 14 and suitably fixed thereto as by tissue adhesive. The separate sections are then fixed in separate washes of formalin, methanol and acetone, and thereafter, treated with a blocking reagent to prevent non-specific binding of the subsequent reagents.

The part of the specimen cells 88 to be measured is incubated with a primary antibody, a monoclonal antibody (rat) to human estrogen receptor in the specimen portion of the slide. This antibody, as represented at 128, binds specifically to the estrogen receptor sites ER of this tissue portion. The reference portion 89 of the specimen is incubated with a control, normal rat IgG, represented at 130. The purpose of the control 130 is to evaluate the amount of binding of the immunoperoxidase reagents in this technique to nonspecific sites NS of the specimen to yield a background measurement.

Both tissue sections 88 and 89 on the slide 102 are then incubated with a bridging antibody, an anti-rat immunoglobulin (goat) illustrated at 132 in both figures. The bridging antibody 132 binds to the rat antibody 128 against human estrogen receptor in the specimen section 88 and to any bound normal rat IgG 130 in the control section 89.

A rat PAP complex 134 is added to both sections 88 and 89 of the specimen and binds to the anti-rat IgG bridging antibody at 132. After this step, a solution containing hydrogen peroxide and diaminobenzidine (DAB) and 4 N HCl is added to the specimen and control sections. The reaction of the peroxidase with hydrogen peroxide converts the bound DAB present into an insoluble reddish brown precipitate. The proportion of the precipitate and its location are influenced by the binding positions of the PAP complex and, through the bridging and primary antibodies, the locations and amounts of the estrogen receptors in the specimen.

The concentrations, timing, and chemical compositions of the reagents used in this staining method are more fully described in the aforementioned U.S. Pat. No. 5,008,185. Preferably, the monoclonal antibody which is used to bind to the estrogen receptor sites is one of those developed at the University of Chicago and designated H222 sP2 and H226 sP2, and that which is used to bind to the progesterone receptor is one which is commercially available from Transbio Sarl 6 Rue Thiers, Paris France and designated mPRl.

The DAB precipitate is then visualized by image analysis with apparatus 10 to determine the quantitation of the estrogen receptors in the specimen. In general, the brown precipitate does not transmit light well and will show up as dark areas in the cells of the specimen. The optical density and hence pixel intensity will be related directly to the amount of DAB precipitate and to the quantity of estrogen receptor which has bound the antibodies. To be able to more clearly visualize the nuclear area of each cell, a counterstain of methyl green is added. It is important to note that both the primary stain of DAB precipitate and the counterstain of methyl green are specific to the nucleus of each cell. This means that debris and other cellular features will appear lighter in the microscope image and can be distinguished.

A dual camera method is thereafter applied to distinguish the areas stained by the DAB and the areas stained by the methyl green. The red and green filters 18 and 24 respectively form monochromatic images of the cell objects at their respective cameras 20 and 26 which images can be stored in the apparatus 10. These images, one by the red filter and the other by the green filter, are used to separate the primary stained areas from the nuclear areas, and to separate the nuclear areas from other cell or field features.

Figure 6:
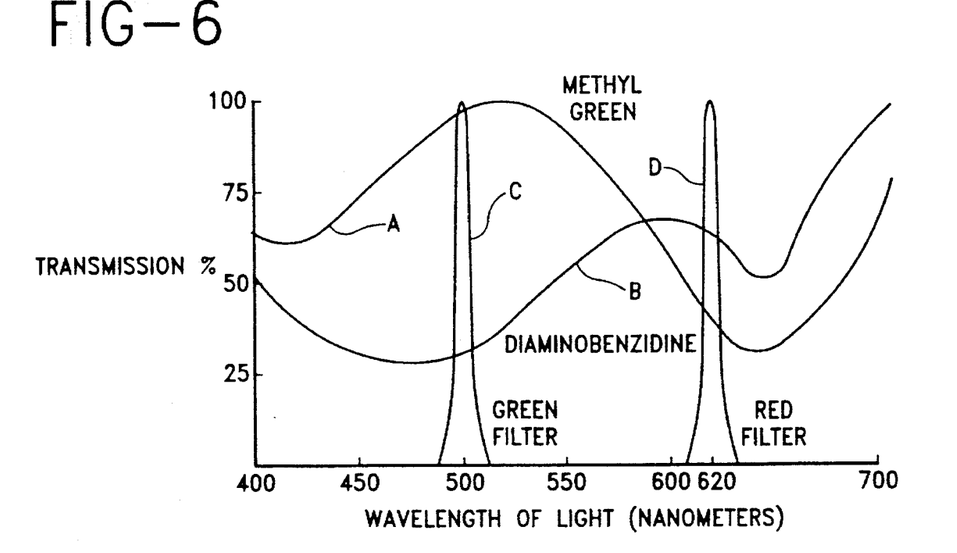
FIG. 6 is a graphical representation of the optical properties employed in biological specimen assay.

The results and desirability of this dual filtering of a counterstained cell image are more fully illustrated in FIG. 6. The percentage of light transmitted through the nuclei stained with methyl green is shown in the curve A as a function of the wavelength of light. The percentage of transmission of light for diaminobenzidine (DAB) is shown in curve B as a function of the wavelength of light. The bandwidth of wavelengths of light passed by the green filter is illustrated in band C while the bandwidth of wavelengths of light passed by the red filter is illustrated in band D.

When an image of a counterstained cell population or specimen is filtered with the green filter 24, substantially all of the areas stained with the methyl green will be invisible. This is because the methyl green curve A has a relative transmissive peak near this wavelength band while the diaminobenzidine curve B is relatively non-transmissive in this band. Thus, the areas with primary DAB stain can be separated from the nuclear areas. At the other extreme of the graph, the band D of the red filter is positioned at a place where just the opposite occurs. The methyl green curve A has a relatively non-transmissive valley in this bandwidth while the diaminobenzidine curve B is also relatively non-transmissive. Thus, the nuclear areas containing both the primary stain and the counterstain appear darker than other cell features and can be readily identified.

Because of the relative differences in light transmission between the primary and counterstain in the two filtered bandwidths, the methyl green stained area is enhanced during one filtering relative to other areas of the cell, and the areas which have diaminobenzidine precipitate are enhanced relative to the methyl green areas during the other filtering. Thus, the nuclear areas of the cell objects are optically enhanced along with the areas having DAB precipitate.

Figure 11:
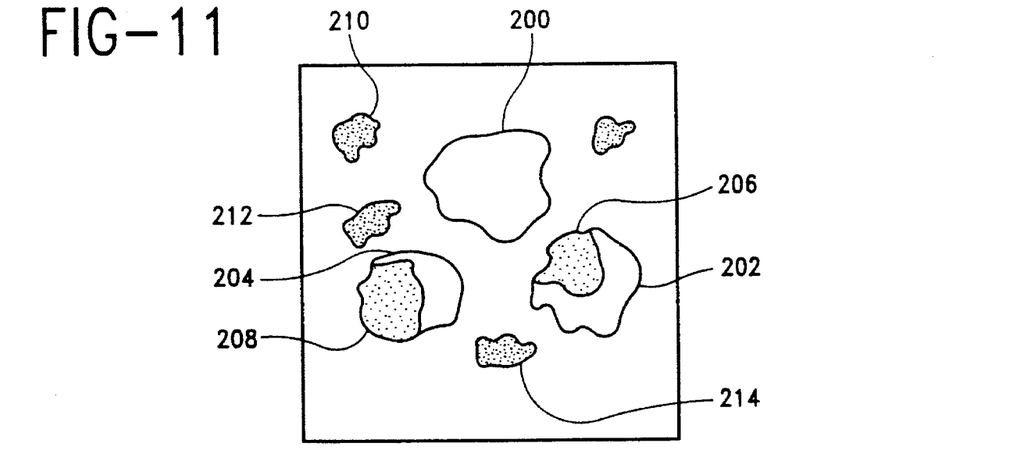
FIG. 11 represents an image field of an optically unfiltered tissue section.
Figure 12:
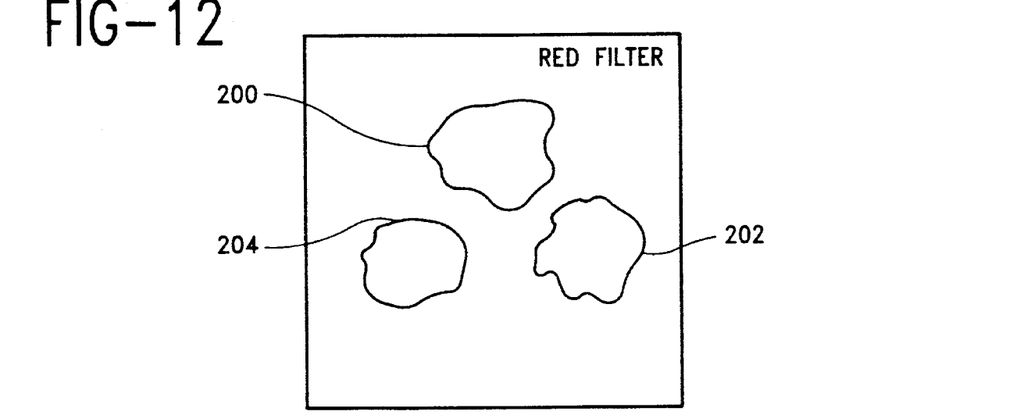
FIG. 12 represents the image field of FIG. 11 when optically filtered by a red filter having a passband centered about 620 nanometers.
Figure 13:
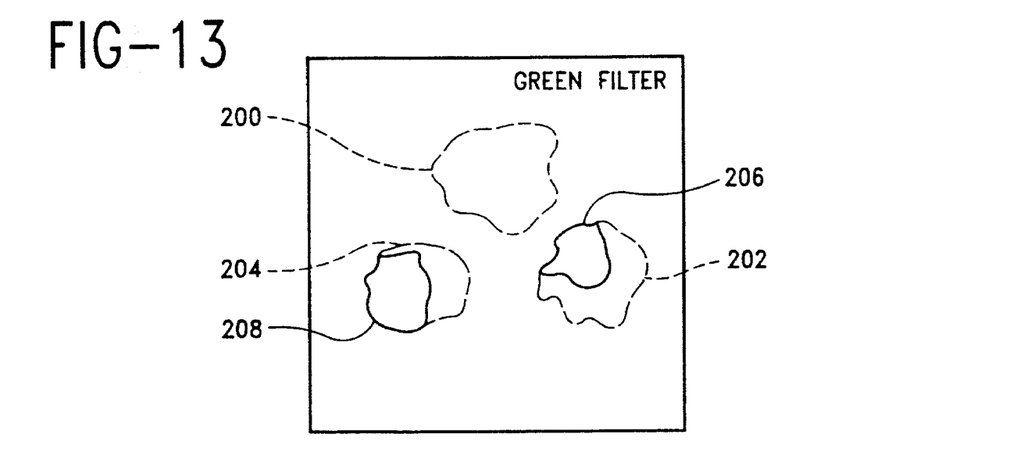
FIG. 13 represents the image field of FIG. 11 when optically filtered by a green filter having a passband centered about 500 nanometers.

FIG. 11 represents an optical image field of a tissue sample as presented to the microscope objective 64. In the image of FIG. 11, objects 200, 202 and 204 are green cell nuclei where nuclei 202 and 204 have brown areas 206 and 208 respectively of DAB precipitate. Nucleus 200 does not contain any estrogen receptor and therefore, does not have any DAB precipitate. Objects 210, 212 and 214 are various other cell features or debris from the tissue section. FIG. 12 represents the image field presented by red filter 18 to camera 20 and its associated image processor 90. In FIG. 12, the nuclei 200, 202 and 204 stand out because of the counter staining and filtering, while the DAB areas are not visible. FIG. 13 represents the image field presented by green filter 24, to camera 26 and its associated image processor 92. In FIG. 13, the estrogen receptor areas 206 and 208 stand out so that their area and density can be readily measured. The dotted lines of FIG. 13 represent the boundaries of nuclei 200, 202 and 204, which are shown for reference purposes. As previously discussed, a monitor 30 is available for displaying image fields of the cell sample. When an image field is to be displayed, microprocessor 36 computes a composite image by summing the image field of image processor 90 (of the type shown in FIG. 12). With the image field of image processor 92 (of the type shown in FIG. 13), the composite image is then stored by microprocessor 36 in the predetermined frame buffer of image processor 92 which is the source of images for monitor 30.

While the implementation shows a convenient and advantageous method for discriminating between the two areas having counterstaining, it is recognized that there are various other staining or optical enhancement methods and filtering methods which can be used to optically enhance one particular area or feature over another cell feature. For the quantitation of the specific hormonal receptors shown (progesterone and estrogen receptors), what is important is to distinguish the nuclear area which contains receptors by the presence of the diaminobenzidine precipitate.

In the preferred embodiment, up to eight slides are analyzed in an automatic analysis session. One of the eight slides (101) is a calibrate slide and the remaining seven slides are preferably prepared using tissue sections from the same tissue mass. The calibrate slide 101 is prepared in the same manner as all other slides, but the tissue sections used are taken from a standard tissue mass having known amounts of estrogen and progesterone receptors. Preferably, all eight slides which are to be analyzed in the same session are fixed and stained in accordance with the above disclosed process as a batch, so that they all undergo substantially the same preparation.

Upon completion of the fixing and staining of the slides 101 through 108, they are inserted into slide holder 62a which secures each slide at a predetermined position on the slide holder. In the present embodiment, calibration slide 101 is placed in the left most position and the slides 102 through 108 are distributed in any order in the remaining seven slide positions. All slides are oriented so that their printed rectangle 87 is at the top as shown in FIG. 3. The slide holder is then inserted into the slide holder base 63 with the printed rectangles away from microscope 12. After placement of the slide holder, the operator signals, by means of keyboard 56, that the analysis is to begin.

Figure 9:
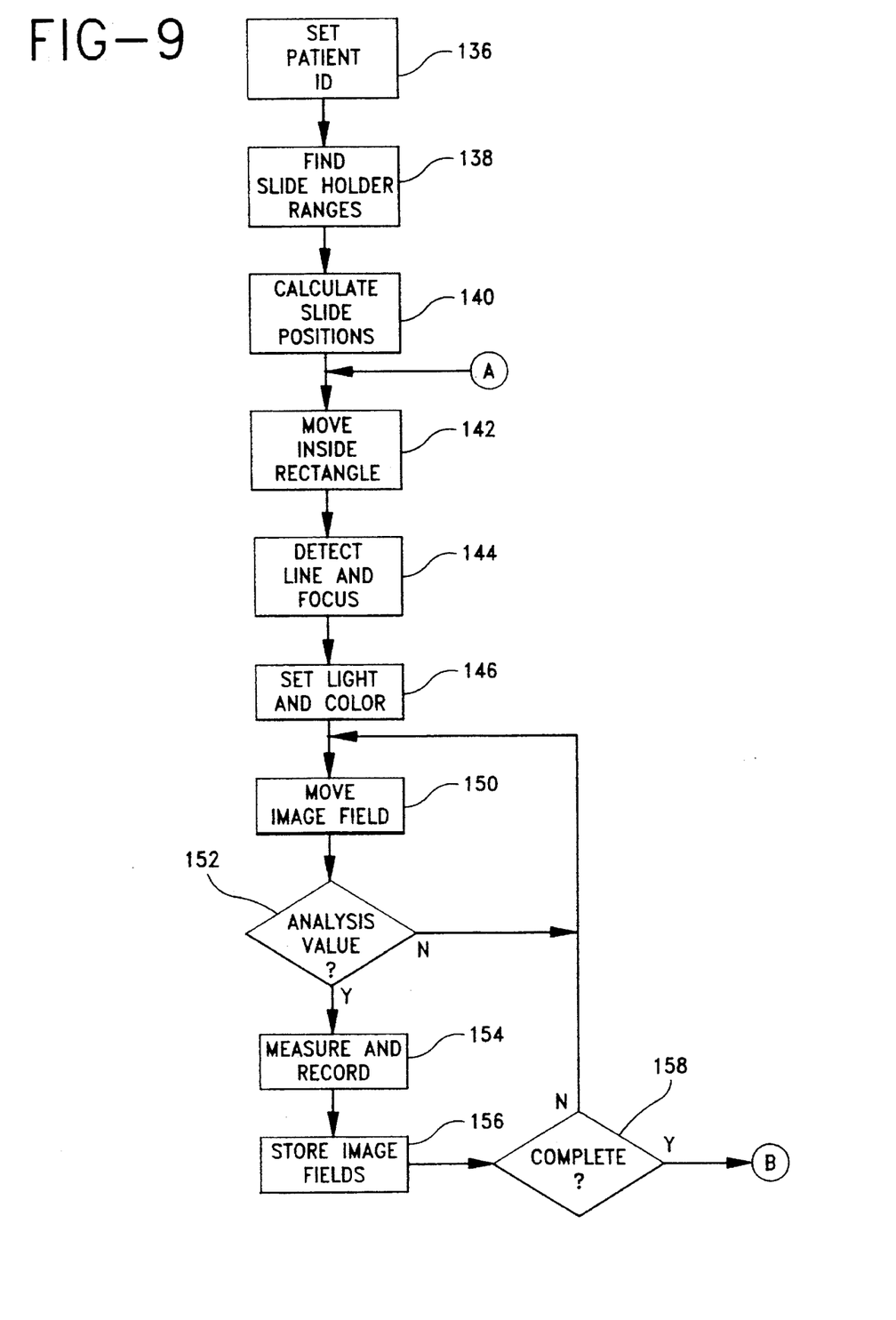
FIGS. 9 and 10 are flow diagrams of the control procedures invoked in the assay of a plurality of biological specimens.
Figure 10:
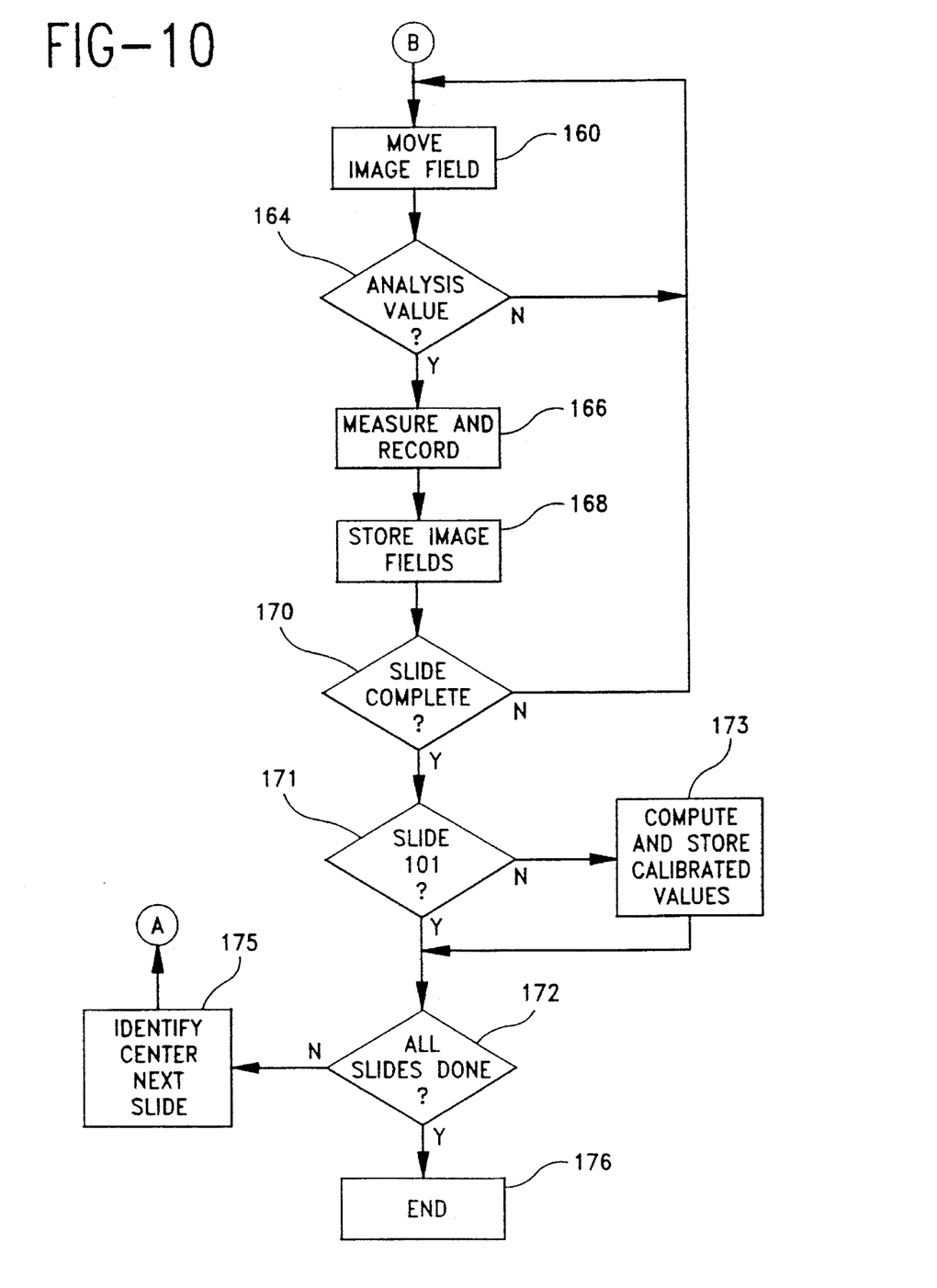

A flow diagram of the automated analysis routine is shown in inter-related FIGS. 9 and 10. The routine begins at a step 136 with a request by the apparatus on instruction monitor 52 for patient labelling information. When patient labelling is completed by means of operator interaction with the keyboard 56, the automated portion of the analysis procedure begins and the operator is free to go about other tasks.

Initially, microprocessor 36 by means of control signals sent over system bus 34 to the slide holder position controller 60, requests the movement of slide holder 62a to its maximum X and Y positions, as represented by a point 120 in the upper left of slide 101 and a point 121 in the lower right of slide 108. No actual marks appear on the slides to represent points 120 and 121, but these points are located by the maximum travel of the slide holder 62a. The X and Y values of points 120 and 121 are read from position sensors 110 and 111 so that the position ranges of slide holder 62a are known by microprocessor 36. Since the slides 101 through 108 are held in predetermined positions, microprocessor 36 can easily compute the X address of the longitudinal center of each slide 101 through 108, and since the position of the rectangle 87 on each slide is also known the Y position of each rectangle 87 can be computed with reasonable accuracy. These slide reference positions are calculated in step 140. The analysis routine next proceeds to step 142 in which the microprocessor 36 requests movement of the slide holder 62 to position the near center of rectangle 87 of slide 101 under the objective 64a.

The automated analysis routine of the present embodiment is performed using a single 40X objective which has a short depth of field on the order of a few microns. Although the slide holder and slides are relatively precise, they do not necessarily guarantee that the surface of the slides will always be at optimum focus when presented to the microscope objective 64a. Accordingly, as the analysis for each new slide begins, the apparatus is first focused using a line 79 of the slide rectangle 87. After the initial focus on line 79 is achieved, the apparatus is periodically refocused during analysis to provide accurate image fields.

In a step 144, the slide 101 is moved so that the path of the objective travels along the imaginary center line 91 (FIG. 5) until line 79 is detected. Line 79 is of sufficient width and capacity that it is detectable even with a poorly focused objective. As the slide 101 moves, microprocessor 36 monitors the pixel array of image processor 90 which represents the current image field presented to the objective. Microprocessor stops slide movement, when line 79 appears in the image field of image processor 90 and performs a focus routine on the inner edge of line 79. In the focus routine microprocessor 36 successively analyses the sharpness of the image field from image processor 40 and adjusts the microscope stage to objective distance by means of focus and light controller 73. When accurate focus is detected by microprocessor 36, the flow proceeds to block 126 in which the slide is moved back to a point within rectangle 87. The rectangle 87 is to be free from any tissue section or other contaminants. Accordingly, the light level and color balance can be adjusted by means described above while the presented image field is from within rectangle 87.

After light level and color balance are established the routine proceeds to a step 150 in which the slide is moved to view successive image fields along the center line 91 in search of a first image field representing reference tissue sample 89. The slide is moved so that the objective 64a traces a path represented by a search path line 94 shown in FIG. 5. Periodically slide motion is stopped, the objective 64a is focused by the microprocessor 36 and the then current image field from image processor 90 is analyzed to determine if the control sample has been found. An image field of control sample 89 will be identified in a step 152 as an image field possessing analysis value. An image field is determined in step 152 to possess analysis value when the area of the nuclear material in the image field from image processor 90 exceeds a predetermined threshold stored in microprocessor 36. Microprocessor 36 analyzes each image field pixel array from image processor 90 which arrays represent the nuclear image of the image fields. When the nuclear area of an image field exceeds the threshold stored in microprocessor 36, the image field has analysis value and the flow proceeds to step 154 where attributes of the image field are measured and recorded.

In step 154, the digitized image field from image processor 90 is analyzed to identify a nuclear boundary level value for the nuclear material in the field. The nuclear boundary level which will be used in quantitation of the specimen 88 is stored in memory 38. Also, in step 154 microprocessor 36 measures the digitized image field from image processor 92 to identify an antibody stain threshold. This threshold is necessary to determine the contribution of the non-specific staining of the control cells and the contribution of the counterstain methyl green, to the total stain detected by the instrument. This antibody stain threshold permits the discrimination between antibody negative stain cells and antibody positive stain cells. After its determination, the antibody stain threshold level is stored in memory 38. Upon completion of the measurement and recording of step 154, a step 156 is performed in which the digital image fields of both image processors 90 and 92 are stored in memory. The digital image fields may advantageously be stored in bulk data drive 45.

The search path 93 (FIG. 5) begins within rectangle 87 and proceeds along center line 91 until a first image field having analysis value is detected at point 93. When microprocessor 36 detects the first control cell object image field, the search movement pattern, directed by microprocessor 36, changes the search movement pattern for image fields, as directed by microprocessor 36, follows a sweeping pattern back and forth across the control as represented in FIG. 5 by the line 94. While traversing the reference specimen 89 successive image fields of the specimen are analyzed and for each image field the possessing analysis value, the nuclear boundary level and the antibody stain threshold are updated. Also, both digital images of each image field found to possess analysis value are stored in memory. Image fields continue to be analyzed from control specimen 89 until the total nuclear area of the image fields of analysis value exceeds 5,000 square microns. When the 5,000 square micron threshold is detected in step 158, slide holder movement is directed to return the objective 64 to center line 91 and to proceed downwardly (step 160) until a first specimen image field is detected at point 96 of FIG. 5. In a manner similar to step 152, the image field having analysis value is identified in step 164 of the flow diagram (FIG. 10) based on the nuclear area contained by the image field.

When step 164 finds an image field having analysis value, the flow proceeds to step 166 where attributes of the specimen image field are measured and recorded. The attributes measured and recorded in step 166 comprise the optical density of DAB areas 206 and 208, the visible area of DAB areas 206 and 208 and a comparison of the total nuclear area in the image field with the area of DAB areas 206 and 208. After measuring and recording image field attributes in step 166, the digitized representations of the image field are also stored in memory. In the present embodiment, the entirety of the specimen 88 is scanned by the apparatus as represented by the line 94 (FIG. 5). The completion of scanning for tissue sample 88 is detected in step 170.

When, as is the case in the present example, the recorded data relates to calibration slide 101, as is detected in step 171, calibration values are calculated and stored for later use in the analysis of measured attributes of other slides 102 through 108. After the storage of the calibrate values in step 173, the flow proceeds to a step 172 to determine if all slides have been analyzed in step 172. Since in the present example, they have not, the slide holder is moved to position the objective in the rectangle 87 of the next slide in the slide set, which is slide 102. In the present example, slides 102 through 108 will be analyzed in sequence in the same manner as calibrate slide 101, except that the data measured in their specimen portions 88 is not stored as calibrate data but as analysis results.

When the last slide 108 has been completely analyzed, the flow diagram of FIGS. 9 and 10 is terminated and the accumulated analysis result data is available for reports as described in detail in the aforementioned U.S. Pat. No. 5,008,185 to Bacus.

In summary, the apparatus 10 includes the interactive optical means 11a which comprises the microscope 12 having multiple turret objectives including a low power objective. The microscope 12 has mounted thereon a manually operable stage for carrying a microscope slide having a biological specimen thereon. The manually operable stage may be manipulated by the operator to bring various portions of the slide under the low power microscope objective. When the operator finds a region of interest, that region is located by the position sensors 12a which are disclosed in U.S. Pat. No. 5,018,209 to Bacus, the content of which is incorporated herein by reference, may be marked by a press of a button on the mouse keyboard signal or the like to signal the processor means that the coordinates of that field are to be stored so that the field may later be examined at high power by the automatic optical means 11b. Thus, the slide may be quickly and rapidly scanned manually at low power selecting the portions of interest and then loaded into the slide rack 62a with other slides for examination at high power by objective 64a using the high speed automatic processing as set forth previously. The low magnification scan of interactive system 11a allows empty fields and fields which are not of interest to be avoided to reduce the amount of time consumed by the automatic optical means 11b. The system 10 therefore provides the advantage of the combination of interactive, rapid, low power scanning and storage of coordinates with high power automatic assay for full diagnostic treatment of the biological specimen.

Further, after the high power assay has been completed, the images may be called up from the WORM drive 45 for additional editing or for deletion from assays, statistics and the like. Thus, the system allows pre-assay editing of the fields by the use of the low power microscope and post-assay editing of the fields with re-assaying by calling up the images from the WORM drive 45.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. An apparatus for automated assay of biological specimens positioned on a plurality of slides of a group, comprising:

operator interactive optical means actuated by an operator for viewing the biological specimen on each of a plurality of slides at a first low magnification and for producing an interactive location signal corresponding to locations of operator selected fields of the viewed image for each of the slides;

means for storing the location signals of the located biological specimens for each of the slides of the group;

means for holding each of the slides of the group and to shift successive selected fields from each of the slides of the group into position for automatic scanning;

automated optical means responsive to said interactive location signal for viewing said selected fields of each of the slides of the group at a second magnification, larger than the first low magnification;

automated means for recognizing each new slide of the group and automatically focusing the automated optical means on each of the slides of the group;

calibrating means for automatically measuring at least one known measurable attribute of a calibration material on at least one slide of the group and for computing a calibration value form said measured attribute value and said known attribute value of said calibration material, said calibration material being located on at least one of the slides of the group;

means for generating an automatic video signal from scanned images of the selected fields;

processing means for processing the automatic video signal for each of the slides of the group to measure said at least one measurable attribute value and correct said at least one measured attribute value in accordance with said computed calibration value for the biological specimens;

said processing means reads the recorded locations, scans the identified locations of the fields and stores image fields corresponding thereto; and said processor means includes means for determining which of a plurality of stored image fields from said automated optical system are selected for biological assay processing.

2. An apparatus for automated assay of biological specimens according to claim 1 further comprising means for automatically adjusting an effective spectral characteristic of light being processed into said automatic video signal.

3. The apparatus in accordance with claim 1 wherein said biological specimen comprises a tissue section sample.

4. The apparatus in accordance with claim 1 wherein said biological specimen comprises a cell sample.

5. An apparatus in accordance with claim 1 wherein said processing means includes:

storing means for storing said computed calibration values and for correcting each of the measured attribute values calculated for each slide of the group in accordance with said computed calibration value.

6. A method of analyzing a plurality of tissue section cell samples, fixed to microscope slides, by means of an image field producing apparatus comprising the steps of:

automatically shifting the slide to position the slide at a substantially known location to bring an opaque target thereon into view;

automatically focusing the image producing means by using the opaque target at the substantially known location;

providing first and second light sensing means for sensing light and producing images for said image field producing apparatus;

adjusting a light source to balance the light sensed by the first and second light sensing means;

automatically adjusting the light intensity in response to a light level sensed by said image producing means;

optically sensing a calibration material on a calibration slide;

optically sensing the tissue section cell samples on the microscope slides;

automatically measuring said at least one known measurable attribute of said calibration material;

computing a calibration value from said at least one measurable attribute of said calibration material and said known quantity of said attribute;

automatically measuring and recording said at least one measurable attribute of the tissue sections cell samples fixed on said tissue sample slides; and correcting the value of the at least one measurable attribute recorded for said tissue section cell samples in accordance with said calibration value.

7. A method in accordance with claim 6 comprising mounting said calibration slide and slides having tissue samples fixed thereto in a slide holder prior to said optical sensing steps.

8. An apparatus for automated assay of biological specimens positioned on a plurality of slides of a group, comprising:

operator interactive optical means actuated by an operator for viewing the biological specimen on each of a plurality of slides at a first low magnification and for producing an interactive location signal corresponding to locations of operator selected fields of the viewed image for each of the slides;

means for storing the location signals of the located biological specimens for each of the slides of the group;

means for holding each of the slides of the group and to shift successive selected fields from each of the slides of the group into position for automatic scanning;

automated optical means responsive to said interactive location signal for viewing said selected fields of each of the slides of the group at a second magnification, larger than the first low magnification;

automated means for recognizing each new slide of the group and automatically focusing the automated optical means on each of the slides of the group;

calibrating means for automatically measuring at least one known measurable attribute of a calibration material on at least one slide of the group and for computing a calibration value form said measured attribute value and said known attribute value of said calibration material, said calibration material being located on at least one of the slides of the group;

means for generating an automatic video signal from scanned images of the selected fields;

processing means for processing the automatic video signal for each of the slides of the group to measure said at least one measurable attribute value and correct said at least one measured attribute value in accordance with said computed calibration value for the biological specimens; and wherein said interactive optical means is a separate and distinct apparatus from said automated optical means.

9. An apparatus for automated assay of biological specimens positioned on a plurality of slides of a group, comprising:

operator interactive optical means actuated by an operator for viewing the biological specimen on each of a plurality of slides at a first low magnification and for producing an interactive location signal corresponding to locations of operator selected fields of the viewed image for each of the slides;

means for storing the location signals of the located biological specimens for each of the slides of the group;

means for holding each of the slides of the group and to shift successive selected fields from each of the slides of the group into position for automatic scanning;

automated optical means responsive to said interactive location signal for viewing said selected fields of each of the slides of the group at a second magnification, larger than the first low magnification;

automated means for recognizing each new slide of the group and automatically focusing the automated optical means on each of the slides of the group;

calibrating means for automatically measuring at least one known measurable attribute of a calibration material on at least one slide of the group and for computing a calibration value form said measured attribute value and said known attribute value of said calibration material, said calibration material being located on at least one of the slides of the group;

means for generating an automatic video signal from scanned images of the selected fields;

processing means for processing the automatic video signal for each of the slides of the group to measure said at least one measurable attribute value and correct said at least one measured attribute value in accordance with said computed calibration value for the biological specimens;

storing means for storing said computed calibration values and for correcting each of the measured attribute values calculated for each slide of the group in accordance with said computed calibration value; and wherein said calibrating means measures at least one measurable attribute of the calibration material only on one slide of the group of slides and the storing means stores the computed calibration value for use by the processing means for correcting the measured attribute values for the remainder of the slides of the group.

10. An apparatus in accordance with claim 9 wherein said processing means includes:

means for optimizing the light intensity of the light source for each recognized new slide of the group.

11. A method for automated assay of biological specimens positioned on a plurality of slides of a group, comprising the steps of:

providing a single slide having calibration material thereon in a group of slides;

substantially simultaneously staining said slides of said group under substantially the same staining conditions;

viewing by an operator an image of the biological specimen on each of said plurality of slides at a first low magnification;

selecting by operator interaction fields of interest from said viewed image;

producing an interactive location signal corresponding to locations of operator selected fields of the viewed image for each of the slides;

storing the location signals of the located biological specimens for each of the slides of the group;

holding each of the slides of the group and shifting, successive selected fields from each of the slides of the group into position for automatic scanning;

automatically viewing said selected fields of each of the slides of the group at a second magnification larger than the first low magnification using automated optical means responsive to said interactive location signal of said selected fields;

automatically recognizing each new slide of the group and automatically focusing the automated optical means on each of the slides of the group;

calibrating by automatically measuring said single slide of the group of slides for at least one measurable attribute of said calibration material and computing a calibration value from said measured attribute value and said known attribute value of said calibration material;

storing the computed calibration value for use by the processing means for correcting the measured attribute values for the remainder of the slides of the group;

generating an automatic video signal from scanned images of the selected fields; and automatically processing the automatic video signal for each of the slides of the group to measure said at least one measurable attribute value and to correct said at least one measured attribute value in accordance with said computed calibration value for the biological specimens.

12. An apparatus for analyzing biological specimens on a plurality of microscope slides comprising:

a slide holder for holding the plurality of microscope slides;

means for producing digital image fields from microscope slides placed in proximity thereto;

means for moving said slide holder to place the biological specimens on the said slides in proximity to said image field producing means without the removal of said slides from said slide holder during image field production; and means for automatically measuring at least one attribute of one of a plurality of digital images produced by said image field producing means from said biological specimens on said plurality of slides, said digital images including digital images from each of said plurality of microscope slides;

focusing means responsive to said digital images from said image producing means for automatically focusing said image producing means on the surface of each of said microscope slides having a biological specimen fixed thereto, said focusing means including, means for producing an image field including a target image and for focusing said image producing means on a target on a surface of the microscope slide having the biological specimen fixed thereto;

a light source;

means for moving said image producing means to a predetermined position with respect to said target;

means for adjusting the light source in response to a light level sensed by said image producing means at said predetermined position;

first light sensing means for sensing a first portion of the light spectrum;

second light sensing means for sensing a second portion of the light spectrum; and, and adjusting means to balance the light sensed by the first and second light sensing means.

* * * * *